(12) United States Patent
Frenche

(10) Patent No.: US 6,565,545 B1
(45) Date of Patent: May 20, 2003

(54) MALE INCONTINENCE DEVICE

(76) Inventor: Adolphe Joseph Frenche, 110 Daimler Dr., Capitol Heights, MD (US) 20743

( * ) Notice: Subject to any disclaimer, the term of this patent is extended or adjusted under 35 U.S.C. 154(b) by 48 days.

(21) Appl. No.: 09/944,027

(22) Filed: Aug. 31, 2001

(51) Int. Cl.$^7$ ............................................. A61F 5/453
(52) U.S. Cl. ................................................... 604/349
(58) Field of Search ................................ 604/327, 346, 604/347, 348, 349, 350, 351, 352, 353, 355, 540, 544, 385.09

(56) References Cited

U.S. PATENT DOCUMENTS

| | | | |
|---|---|---|---|
| 1,389,531 A | | 8/1921 | Riche |
| 2,494,477 A | | 1/1950 | Kurtz |
| 2,640,484 A | * | 6/1953 | Johnson ................ 604/350 |
| 3,292,626 A | * | 12/1966 | Schneider ............. 604/347 |
| 3,295,145 A | * | 1/1967 | Ericson .................. 4/144.3 |
| 3,523,537 A | * | 8/1970 | Hill ........................ 600/574 |
| 3,526,227 A | * | 9/1970 | Applebaum ........... 604/350 |
| 3,547,123 A | * | 12/1970 | Sachs ..................... 604/352 |
| 4,022,213 A | * | 5/1977 | Stein ...................... 604/350 |
| 4,387,726 A | * | 6/1983 | Denard .................. 600/573 |
| 4,553,968 A | | 11/1985 | Komis |
| D288,485 S | | 2/1987 | Denno |
| 4,673,401 A | * | 6/1987 | Jensen et al. ......... 604/353 |
| 4,713,066 A | | 12/1987 | Komis |
| 4,804,377 A | * | 2/1989 | Hanifl et al. ......... 604/352 |
| 5,009,649 A | | 4/1991 | Goulter et al. |
| 5,336,211 A | * | 8/1994 | Metz ...................... 604/352 |
| 5,368,583 A | * | 11/1994 | Fleury ................... 604/318 |
| 5,380,312 A | * | 1/1995 | Goulter ................. 604/352 |
| 6,152,903 A | * | 11/2000 | Falconer ............... 604/351 |
| 6,336,920 B1 | * | 1/2002 | Temple .................. 604/355 |

* cited by examiner

*Primary Examiner*—Weilun Lo
*Assistant Examiner*—Michael Bogart

(57) ABSTRACT

A male incontinence device for removably fitting on an end of a user's penis. The device is releasably couplable to underwear having a waistband worn by the user. The male incontinence device includes a housing that has a front wall and a back wall defining an interior of the housing. The back wall of the housing has an access opening for providing access to the interior of the housing. In one embodiment of the present invention, the end of a penis is inserted into the interior of the housing through the access opening. An intermediate wall is mounted in the interior of the housing dividing the interior into an upper compartment and a lower compartment. In one embodiment of the present invention, the end of the penis is positioned in the upper compartment such that urine flows from the penis into the lower compartment of the housing.

14 Claims, 2 Drawing Sheets

MALE INCONTINENCE DEVICE

BACKGROUND OF THE INVENTION

1. Field of the Invention

The present invention relates to incontinence devices and more particularly pertains to a new male incontinence device for removably fitting on an end of a user's penis. The device is releasably couplable to underwear having a waistband worn by the user.

2. Description of the Prior Art

The use of incontinence devices is known in the prior art. More specifically, incontinence devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,713,066; 4,553,968; 5,009,649; 1,389,531; 2,494,477; and U.S. Pat. No. Des. 288,485; and U.S. Pat. No. 7777.

While these devices fulfill their respective, particular objectives and requirements, the aforementioned patents do not disclose a new male incontinence device. The inventive device includes a housing that has a front wall and a back wall defining an interior of the housing. The back wall of the housing has an access opening for providing access to the interior of the housing. In one embodiment of the present invention, the end of a penis is inserted into the interior of the housing through the access opening. An intermediate wall is mounted in the interior of the housing dividing the interior into an upper compartment and a lower compartment. In one embodiment of the present invention, the end of the penis is positioned in the upper compartment such that urine flows from the penis into the lower compartment of the housing.

In these respects, the male incontinence device according to the present invention substantially departs from the conventional concepts and designs of the prior art, and in so doing provides an apparatus primarily developed for the purpose of removably fitting on an end of a user's penis. The device is releasably couplable to underwear having a waistband worn by the user.

SUMMARY OF THE INVENTION

In view of the foregoing disadvantages inherent in the known types of incontinence devices now present in the prior art, the present invention provides a new male incontinence device construction wherein the same can be utilized for removably fitting on an end of a user's penis. The device is releasably couplable to underwear having a waistband worn by the user.

The general purpose of the present invention, which will be described subsequently in greater detail, is to provide a new male incontinence device apparatus and method which has many of the advantages of the incontinence devices mentioned heretofore and many novel features that result in a new male incontinence device which is not anticipated, rendered obvious, suggested, or even implied by any of the prior art incontinence devices, either alone or in any combination thereof.

To attain this, the present invention generally comprises a housing that has a front wall and a back wall defining an interior of the housing. The back wall of the housing has an access opening for providing access to the interior of the housing. In one embodiment of the present invention, the end of a penis is inserted into the interior of the housing through the access opening. An intermediate wall is mounted in the interior of the housing dividing the interior into an upper compartment and a lower compartment. In one embodiment of the present invention, the end of the penis is positioned in the upper compartment such that urine flows from the penis into the lower compartment of the housing.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new male incontinence device apparatus and method which has many of the advantages of the incontinence devices mentioned heretofore and many novel features that result in a new male incontinence device which is not anticipated, rendered obvious, suggested, or even implied by any of the prior art incontinence devices, either alone or in any combination thereof.

It is another object of the present invention to provide a new male incontinence device which may be easily and efficiently manufactured and marketed.

It is a further object of the present invention to provide a new male incontinence device which is of a durable and reliable construction.

An even further object of the present invention is to provide a new male incontinence device which is susceptible of a low cost of manufacture with regard to both materials and labor, and which accordingly is then susceptible of low prices of sale to the consuming public, thereby making such male incontinence device economically available to the buying public.

Still yet another object of the present invention is to provide a new male incontinence device which provides in the apparatuses and methods of the prior art some of the advantages thereof, while simultaneously overcoming some of the disadvantages normally associated therewith.

Still another object of the present invention is to provide a new male incontinence device for removably fitting on an end of a user's penis. The device is releasably couplable to underwear having a waistband worn by the user.

Yet another object of the present invention is to provide a new male incontinence device which includes a housing that has a front wall and a back wall defining an interior of the housing. The back wall of the housing has an access opening for providing access to the interior of the housing. In one embodiment of the present invention, the end of a penis is inserted into the interior of the housing through the access opening. An intermediate wall is mounted in the interior of the housing dividing the interior into an upper compartment and a lower compartment. In one embodiment of the present invention, the end of the penis is positioned in the upper compartment such that urine flows from the penis into the lower compartment of the housing.

Still yet another object of the present invention is to provide a new male incontinence device that permits a user to enjoy more activities without the worry of an uncontrollable bladder.

Even still another object of the present invention is to provide a new male incontinence device that is more comfortable and less bulky than conventional male incontinence devices. The present invention separates the penis from the urine collected providing a more hygienic device.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
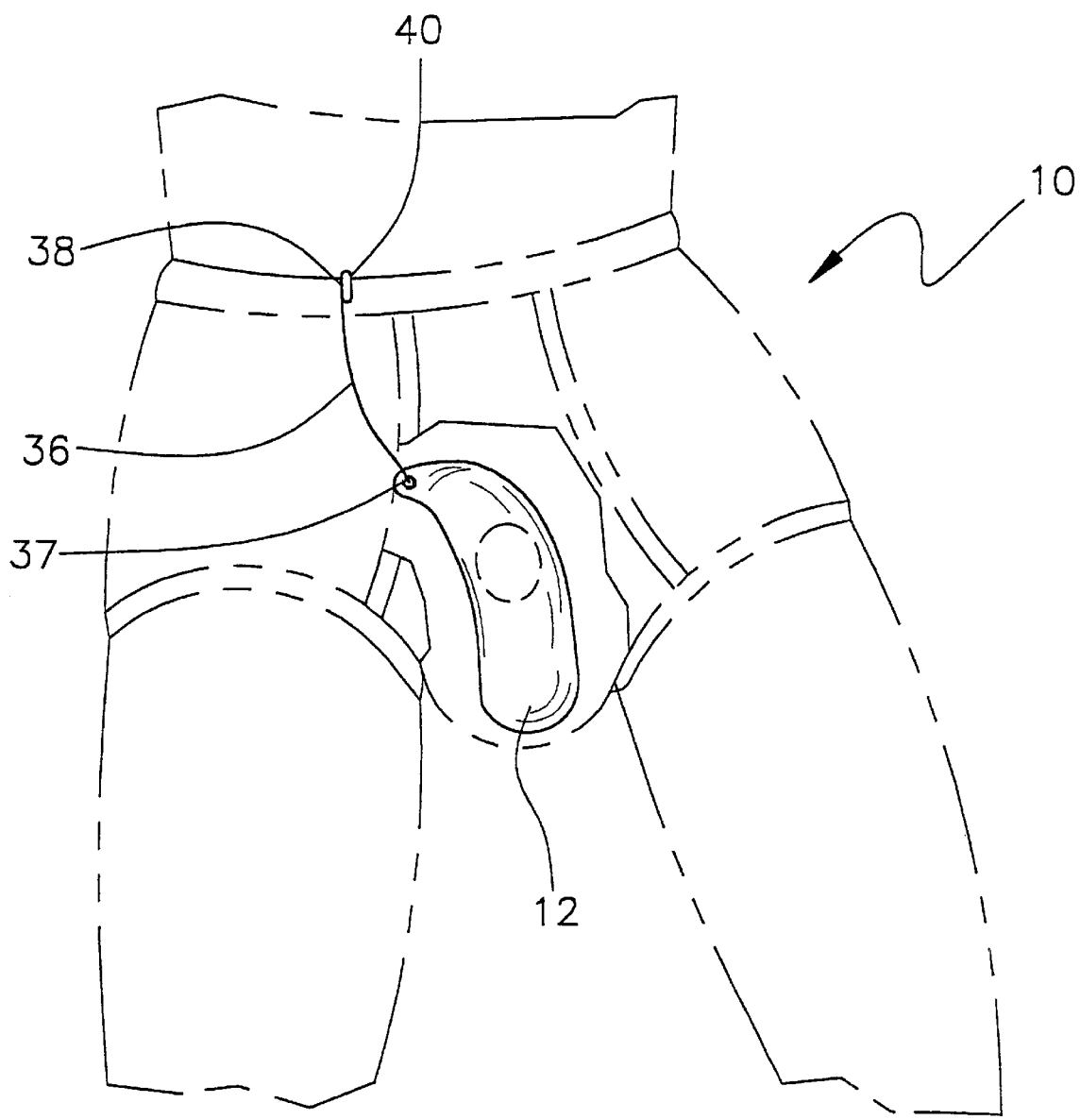
FIG. 1 is a schematic frontal view of a new male incontinence device according to the present invention.
Figure 2:
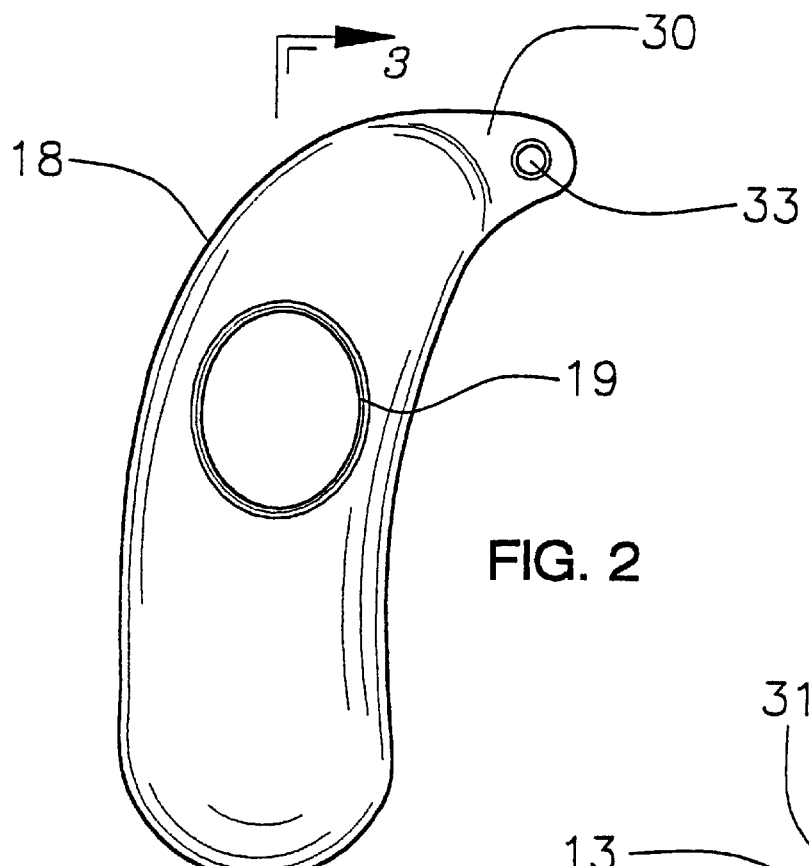
FIG. 2 is a schematic rear view of the present invention.
Figure 3:
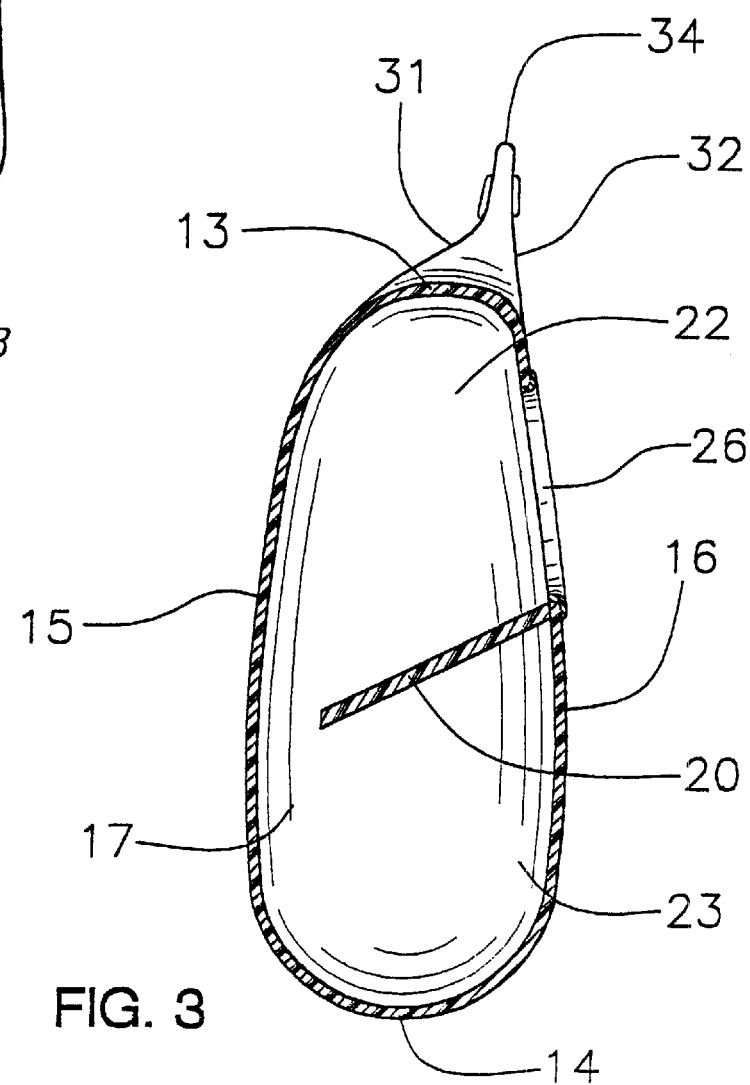
FIG. 3 is a schematic cross sectional view of the present invention taken along line 3—3 of FIG. 2.

With reference now to the drawings, and in particular to FIGS. 1 through 3 thereof, a new male incontinence device embodying the principles and concepts of the present invention and generally designated by the reference numeral 10 will be described.

As best illustrated in FIGS. 1 through 3, the male incontinence device 10 generally comprises a housing 12 that has a first end 13, a second end 14, a front wall 15 and a back wall 16. The front 15 and back 16 walls define an interior 17 of the housing 12. The housing 12 may have a longitudinal axis extending between the first 15 and second 16 ends of the housing 12. As illustrated in FIGS. 1 and 2, the housing 12 may have a bend 18 such that the first end 13 of the housing 12 is askew from the longitudinal axis of the housing 12.

The back wall 16 of the housing 12 has an access opening 19 for providing access to the interior 17 of the housing 12. In one embodiment of the present invention, the end of a penis is inserted into the interior 17 of the housing 12 through the access opening 19.

The housing 12 may comprise a substantially flexible material such as, for example, a latex or natural rubber material. However, other types of materials may also be employed.

As particularly illustrated in FIG. 3, an intermediate wall 20 is mounted in the interior 17 of the housing 12 dividing the interior 17 into an upper compartment 22 and a lower compartment 23. In one embodiment of the present invention, the end of the penis is positioned in the upper compartment 22.

The intermediate wall 20 is mounted to an inner surface of the back wall 16 and may extend generally perpendicular to the longitudinal axis of the housing 12 toward the front wall 15 and the second end 14 of the housing 12. The intermediate wall 20 may comprise a resiliently flexible material such as, for example, a latex, or natural rubber material.

An annular member 26 may be mounted to the back wall 16 of the housing 12 for removably securing the housing 12 onto the end of a user's penis. The annular member 26 is mounted about the access opening 19 of the housing 12. The annular member 26 preferably comprises a generally flexible material such as, for example, a natural rubber or plastic material.

As illustrated in FIGS. 1, 2 and 3, a tab member 30 is mounted to the first end 13 of the housing 12 for securing the housing 12 to a waistband of underwear worn by a user. The tab member 30 has an outer surface 31 and an inner surface 32. The inner 32 and outer 31 surfaces of the tab member 30 have an aperture 33 extending therethrough.

The tab member 30 has a width extending between the outer 31 and inners 32 surfaces of the tab member 30. In one embodiment of the present invention, the width of the tab member 30 may taper from the first end 13 of the housing 12 toward an end 34 of the tab member 30.

As illustrated in FIG. 1, a coupling member 36 may extend between and may be removably couplable to the housing 12 and the waistband of the underwear worn by a user. The coupling member 36 has a first end 37 and a second end 38. The first end 37 of the coupling member 36 extends through the aperture 33 of the tab member 30 and is coupled thereto.

A securing means 40 may be mounted on the second end 38 of the coupling member 36 for releasably securing the coupling member 36 to the waistband of the underwear. The securing means 40 may comprise an alligator clip or any type of securing means capable of securing the second end 38 of the coupling member 36 to the waistband of the underwear worn by a user.

In use, the housing 12 is worn on the end of a penis. The end of the penis is positioned in the upper compartment 22 of the housing. When a user urinates the urine flows down the intermediate wall 20 and flows into the lower compartment 23 of the housing 12. The intermediate wall 20 prevents the urine in the lower compartment 23 from entering the upper compartment 22.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A male incontinence device for removably fitting on an end of a user's penis, the device being releasably couplable to underwear having a waistband worn by the user, said device comprising:

a housing having a front wall and a back wall defining an interior of said housing;

said back wall of said housing having an access opening for providing access to said interior of said housing, wherein the end of a penis is inserted into said interior of said housing through said access opening;

an intermediate wall being mounted in said interior of said housing dividing said interior into an upper compartment and a lower compartment, wherein the end of the penis is positioned in said upper compartment, wherein urine flows from the penis to said lower compartment of said housing;

wherein said housing has a first end, a second end, a longitudinal axis extending between said first end second ends of said housing; and wherein said housing has a bend such that said first end of said housing is askew from said longitudinal axis of said housing.

2. The male incontinence device of claim 1, wherein said housing comprises a substantially flexible material.

3. The male incontinence device of claim 1, wherein said intermediate wall is mounted to an inner surface of said back wall and extends generally perpendicular to a longitudinal axis of said housing toward said front wall and toward a second end of said housing.

4. The male incontinence device of claim 3, wherein said intermediate wall comprises a generally flexible material.

5. The male incontinence device of claim 1, additionally including an annular member being mounted about said opening of said back wall of said housing for providing a snug fit of said housing about the penis of a user.

6. The male incontinence device of claim 5, wherein said annular member comprises a substantially flexible material.

7. The male incontinence device of claim 1, additionally including a tab member being mounted to a first end of said housing for securing said housing to the waistband of the underwear.

8. The male incontinence device of claim 7, wherein said tab member has an outer surface and an inner surface, said tab member having a width extending between said outer and inners surfaces of said tab member, said width of said tab member tapering from said first end of said housing toward an end of said tab member.

9. The male incontinence device of claim 8, wherein said inner and outer surfaces of said tab member having an aperture extending therethrough; and a coupling member extending between and being removably couplable to said housing and the waistband of the underwear, said coupling member having a first end being extended through said aperture of said tab member and coupled thereto.

10. The male incontinence device of claim 9, additionally including a securing means being mounted on a second end of said coupling member for releasably coupling said coupling member to the waistband of the underwear.

11. A male incontinence device for removably fitting on an end of a user, the device being releasably couplable to a waistband of a pair of underwear, said device comprising:

a housing having a first end, a second end, a front wall and a back wall, said front and back walls defining an interior of said housing, said housing having a longitudinal axis extending between said first and second ends of said housing;

said housing having a bend such that said first end of said housing being askew from said longitudinal axis of said housing;

said back wall of said housing having an access opening for providing access to said interior of said housing, wherein the end of a penis is inserted into said interior of said housing through said access opening;

said housing comprising a substantially flexible material;

an intermediate wall being mounted in said interior of said housing dividing said interior into an upper compartment and a lower compartment, wherein the end of the penis is positioned in said upper compartment;

said intermediate wall being mounted to an inner surface of said back wall and extending generally perpendicular to said longitudinal axis of said housing toward said front wall and said second end of said housing, wherein urine flows down said intermediate wall and into said lower compartment of said housing;

an annular member being mounted to said back wall of said housing for snuggly fitting said housing onto the end of a penis, said annular member being about said access opening;

said annular member comprising a flexible material;

a tab member being mounted to said first end of said housing for securing said housing to the waistband of the underwear worn by a user, said tab member having an outer surface and an inner surface, said inner and outer surfaces of said tab member having an aperture extending therethrough;

said tab member having a width extending between said outer and inners surfaces of said tab member, said width of said tab member tapering from said first end of said housing toward and end of said tab member;

a coupling member extending between and being removably couplable to said housing and the waistband of the underwear, said coupling member having a first end and a second end, said first end being extended through said aperture of said tab member and coupled thereto; and a securing means being mounted on said second end of said coupling member for releasably coupling said coupling member to the waistband of the underwear.

12. A male incontinence device for removably fitting on an end of a user's penis, the device being releasably couplable to underwear having a waistband worn by the user, said device comprising:

a housing having a front wall and a back wall defining an interior of said housing;

said back wall of said housing having an access opening for providing access to said interior of said housing, wherein the end of a penis is inserted into said interior of said housing through said access opening;

an intermediate wall being mounted in said interior of said housing dividing said interior into an upper compartment and a lower compartment, wherein the end of the penis is positioned in said upper compartment, wherein urine flows from the penis to said lower compartment of said housing;

a tab member being mounted to a first end of said housing for securing said housing to the waistband of the underwear; and wherein said tab member has an outer surface and an inner surface, said tab member having a width extending between said outer and inners surfaces of said tab member, said width of said tab member tapering from said first end of said housing toward an end of said tab member.

13. The male incontinence device of claim 12, wherein said inner and outer surfaces of said tab member having an aperture extending therethrough; and a coupling member extending between and being removably couplable to said housing and the waistband of the underwear, said coupling member having a first end being extended through said aperture of said tab member and coupled thereto.

14. The male incontinence device of claim 13, additionally including a securing means being mounted on a second end of said coupling member for releasably coupling said coupling member to the waistband of the underwear.

* * * * *